United States Patent
Castle

(10) Patent No.: US 9,301,868 B2
(45) Date of Patent: Apr. 5, 2016

(54) LEG SUPPORT PILLOW

(71) Applicant: Leona Castle, Cumberland (CA)

(72) Inventor: Leona Castle, Cumberland (CA)

( * ) Notice: Subject to any disclaimer, the term of this patent is extended or adjusted under 35 U.S.C. 154(b) by 270 days.

(21) Appl. No.: 13/797,081

(22) Filed: Mar. 12, 2013

(65) Prior Publication Data

US 2013/0319426 A1     Dec. 5, 2013

(30) Foreign Application Priority Data

Jun. 5, 2012   (CA) ....................................... 2779440

(51) Int. Cl.
| | | |
|---|---|---|
| *A61G 15/00* | (2006.01) | |
| *A61F 5/30* | (2006.01) | |
| *A61G 7/075* | (2006.01) | |

(52) U.S. Cl.
CPC ................ *A61F 5/30* (2013.01); *A61G 7/0755* (2013.01)

(58) Field of Classification Search
CPC ....... A61G 13/04; A61G 13/06; A61G 13/08; A61G 13/0036; A61G 13/02; A61G 2005/127; A61G 2013/0054; A61G 5/006; A61G 5/10; A61G 5/1005; A61G 5/101; A61G 5/1021; A61G 5/1035; A61G 5/1059; A61G 7/0755; A61F 5/30
USPC .................. 128/845, 882; 602/23–27, 60–62; 5/624, 648, 650, 651
See application file for complete search history.

(56) References Cited

U.S. PATENT DOCUMENTS

| | | | | |
|---|---|---|---|---|
| 2,581,110 | A * | 1/1952 | Kenworthy | 297/423.46 |
| 3,481,593 | A * | 12/1969 | Doermann et al. | 5/648 |
| 3,532,336 | A * | 10/1970 | Baker | 5/650 |
| 4,584,730 | A | 4/1986 | Rajan | |
| 5,117,522 | A | 6/1992 | Everett | |
| 5,716,334 | A * | 2/1998 | Wade | 602/6 |
| 5,725,486 | A | 3/1998 | Engelman | |
| 8,156,941 | B1 * | 4/2012 | Simms | 128/882 |
| 2010/0087765 | A1 * | 4/2010 | Gainey | 602/23 |
| 2010/0200001 | A1 * | 8/2010 | Randall | 128/845 |

* cited by examiner

*Primary Examiner* — Michael Brown
(74) *Attorney, Agent, or Firm* — Stites & Harbison, PLLC; David W. Nagle, Jr.

(57) ABSTRACT

A leg support pillow apparatus for supporting a lower leg and foot of a person lying in a bed has a base with a first thickness at an upper knee end thereof and an increased second thickness at a lower foot end thereof. Partition walls extend upward from the base and define leg channels extending from the knee end to the foot end of the base. The channels include foot portions at foot ends thereof having a width and depth configured to support the feet in an upright orientation, and upper knee ends of the channels have a width greater than the foot portions. Heel openings in the base under lower ends of each foot portion of the channels are configured such that when the leg is resting on the base inside the channel, the heel extends down into the heel opening and is supported above the bed.

15 Claims, 2 Drawing Sheets

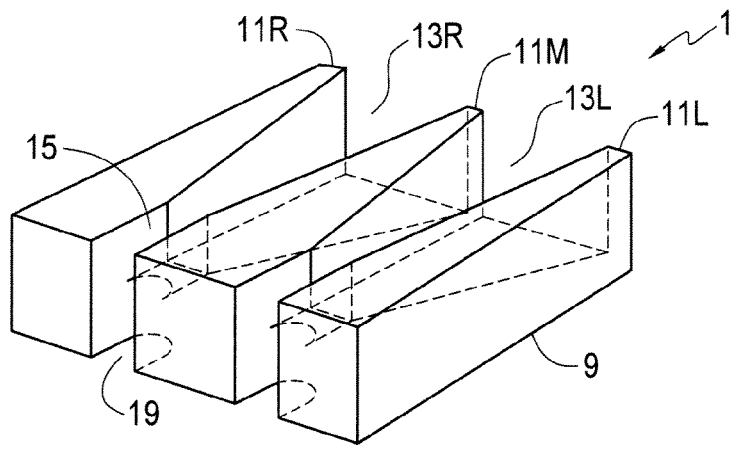
FIG. 5
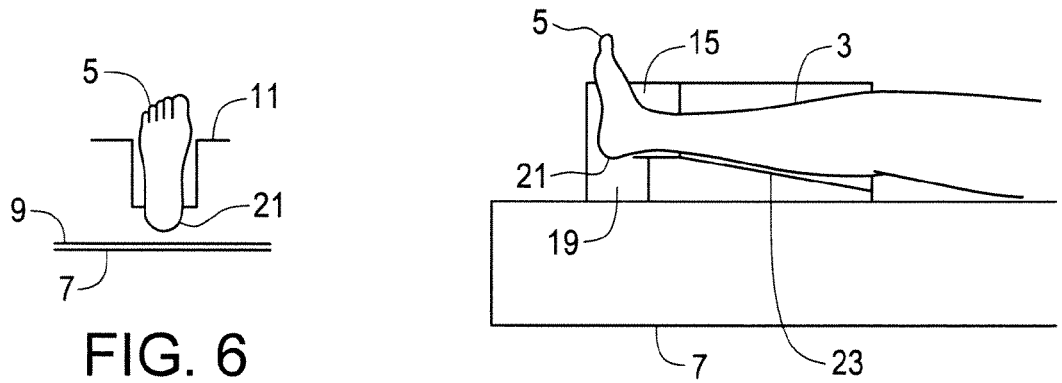
FIG. 6
FIG. 7
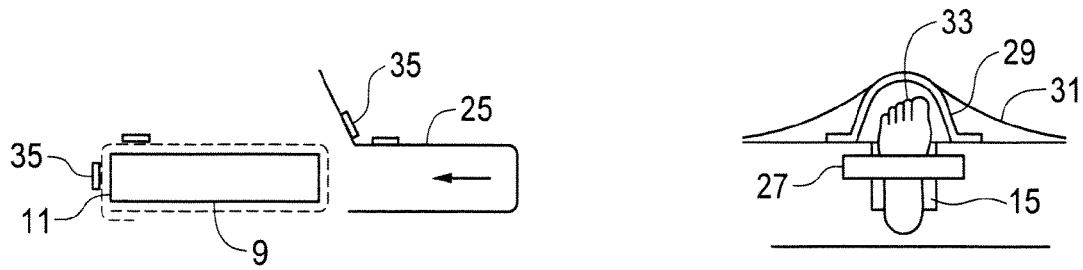
FIG. 8
FIG. 9

LEG SUPPORT PILLOW

This invention is in the field of patient care equipment and in particular a support pillow for the legs of immobile patients that relieves pressure on the heels while supporting the feet.

BACKGROUND

Some medical conditions require extended periods of bed rest. During these extended periods of immobility, pressure ulcers commonly occur on areas of the body that are in contact with the bed. Pillows, rolled up blankets, and the like are often used to prop the torso or extremities in varying positions to relieve this pressure, however it is difficult to keep these in place, and so various support devices have been developed to more securely support the patient.

For example, U.S. Pat. No. 8,156,941 to Simms discloses a heel offloading abductor pillow to relieve pressure from a post-surgical hip patient's heels while supporting the patient's legs. U.S. Pat. No. 5,725,486 to Engelman discloses an orthotic leg elevator for elevating the leg of a subject in situations in which it is necessary to avoid direct contact between the leg and a bed or other surface, or to raise the leg with respect to a surface. U.S. Pat. No. 5,117,522 to Everett discloses a leg pillow for use in supporting the legs of a person in bed. U.S. Pat. No. 4,584,730 to Rajan discloses a device for stabilizing the pelvis of a lying patient in a preselected angular position relative to a conventional flat bed.

SUMMARY OF THE INVENTION

It is an object of the present invention to provide a leg support pillow that overcomes problems in the prior art.

The present invention provides a leg support pillow apparatus for supporting a lower leg and foot of a person lying in a bed. The apparatus comprises a base having a first thickness at an upper knee end thereof and an increased second thickness at a lower foot end thereof, and partition walls extending upward from the base and defining at least one leg channel extending substantially from the knee end to the foot end of the base. The at least one leg channel includes a foot portion at a foot end thereof having a width and depth configured to support the foot in a substantially upright orientation, and wherein an upper knee end of the at least one leg channel has a width greater than the width of the foot portion. A heel opening in the base under a lower end of the foot portion of the at least one leg channel is configured such that when the leg is resting on the base inside the at least one leg channel, the heel extends down into the heel opening and is supported above the bed.

The pillow may be provided in a single version with a single leg channel, or a double version for both legs with two channels. A recess may be provided in the base between the heel and foot ends thereof to relieve pressure on the calf.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

FIG. 5 is a schematic perspective view of the embodiment of FIG. 1;

FIG. 6 is a schematic end view of the bottom of a foot supported in the embodiment of FIG. 1;

FIG. 7 is a schematic cut away side view of the supported foot and leg of FIG. 6;

FIG. 8 is a schematic side view of a removable and washable pillow cover for the embodiment of FIG. 1; and FIG. 9 is a schematic end view of the embodiment of FIG. 1 with a foot drop strap and foot cage attached.

DETAILED DESCRIPTION OF THE ILLUSTRATED EMBODIMENTS

Figure 1:
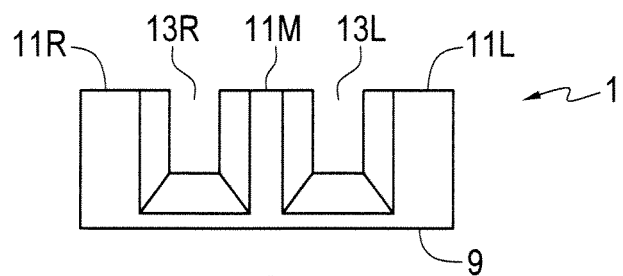
FIG. 1 is a schematic end view of an embodiment of a leg support pillow apparatus of the present invention, seen from the upper knee end of the apparatus.
Figure 2:
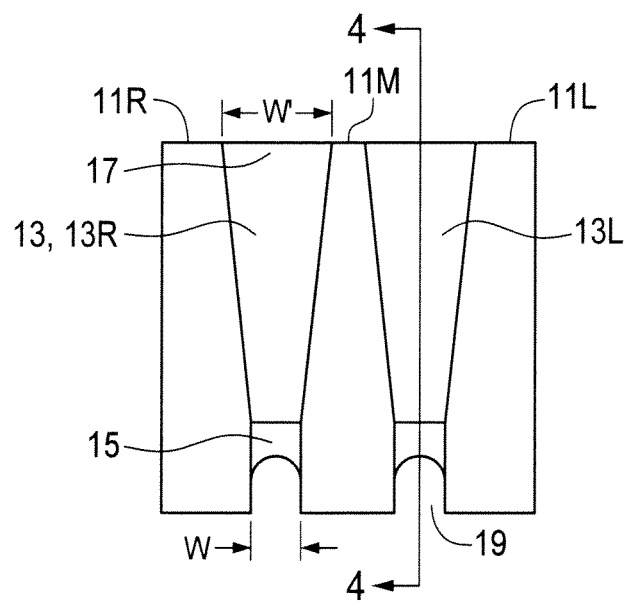
FIG. 2 is a schematic top view of the embodiment of FIG. 1.
Figure 4:
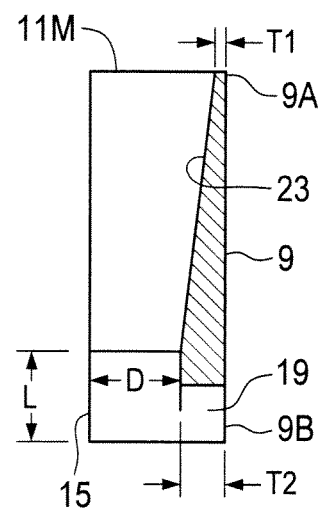
FIG. 4 is a schematic sectional side view of the embodiment of FIG. 1 taken along line 4-4 in FIG. 2.
Figure 3:
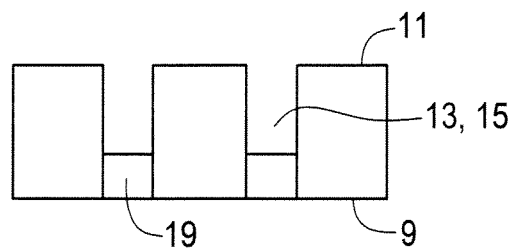
FIG. 3 is a schematic end view of the embodiment of FIG. 1 seen from the lower foot end of the apparatus.

FIGS. 1-5 schematically illustrate an embodiment of a leg support pillow apparatus 1 of the present invention for supporting a lower leg 3 and foot 5 of a person lying in a bed 7, as schematically illustrated in FIGS. 6 and 7.

The apparatus 1 comprises a base 9 having a first thickness T1 at an upper knee end 9A thereof and an increased second thickness T2 at a lower foot end 9B thereof. Right, left, and middle partition walls 11R, 11L, 11M1 extend upward from the base 9 and define right and left leg channels 13R, 13L extending substantially from the knee end 9A to the foot end 9B of the base 9. The apparatus 1 is for two legs, but where it is desired to support one leg only, a single version can be provided with a single leg channel.

The leg channels 13 include a foot portion 15 at a foot end thereof having a width W and depth D configured to support the foot 5 in a substantially upright orientation as seen in FIGS. 6 and 7. The upper knee end 17 of the leg channels 13 have a width W' that is greater than the width W of the foot portion 15, to accommodate the wider portion of the lower leg 3.

A heel opening 19 in the base 9 under a lower end of the foot portion 15 of the leg channels 13 is configured such that when a leg 3 is resting on the base 9 inside a leg channel 13, the heel 21 extends down into the heel opening 19 and is supported above the bed 7, and so is not in contact with anything, and so is not subject to pressure. At the same time the foot 5 is maintained in a comfortable upright position by the partition walls 11 so same does not flop to one side or the other.

The floor 23 of each leg channel tapers upward from the knee end 17 thereof to the foot portion 15 thereof, providing a comfortable support for the lower leg 3. A recess can be provided in a middle portion of the floor 23 to relieve pressure on the calf of the leg if desired.

While the measurements could be selected to suit a particular patient, it is contemplated that in a typical pillow apparatus 1 of the invention the foot portions 15 of the leg channels have a width W of about 2.5 inches to 3.5 inches, a depth D of about five inches to eight inches, and a length L of about three inches to about five inches. The heel recesses 19 extend from the foot end 9B of the base 9 about 3 inches to 5 inches up the leg channels 13, and the distance from the knee end 9A to the foot end 9B of the base 9 is about 21 inches to about 25 inches.

These dimensions should accommodate the majority of leg sizes, and allow for the economical production of pillow apparatuses 1 in standard sizes.

The base 9 and partition walls 11 are made from a resilient material, such as a sponge or foam material that is soft enough to conform to the leg for comfort but still hard enough to also provide the required support for the foot.

As schematically illustrated in FIG. 8, for cleanliness, a removable and washable pillow cover 25 is provided and configured to conform to at least a top portion of the base 9, the partition walls 11, and the leg channels 13, where the patient's legs will be in contact with the apparatus 1.

As schematically illustrated in FIG. 9, a foot drop strap 27 can be attached across a lower end of the foot portion 15 such that the foot drop strap bears against a bottom of the foot 5 preventing the foot from dropping forward, and supporting the foot 5 in a substantially upright orientation. FIG. 9 also shows a foot cage 29 adapted to be attached over the foot portion 15 to a sheet 31 above toes 33 of the foot 5. Conveniently a hook and loop fastener such as Velcro® can be used. Where a pillow cover 25 as shown in FIG. 8 is used, one part 35 of the hook and loop fastener can be attached to the pillow cover 25 and the other part to the foot drop strap 27 and/or cage 29.

The leg pillow apparatus 1 of the present invention provides improved comfort for immobile persons lying on their back by supporting the feet in an upright orientation with the heel suspended in mid-air. It is contemplated as well that by moving the pillow apparatus 1 upward somewhat, the feet 5 will move down out of the foot portions 15 of the leg channels 13, and allow the person, for a change and increased comfort, to turn on the side with the feet turning laterally below the apparatus 1, and the legs 3 in the channels 13.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

What is claimed is:

1. A leg support pillow apparatus for supporting a lower leg and foot of a person lying in a bed, the apparatus comprising:
    a base having a first thickness at an upper knee end thereof and an increased second thickness at a lower foot end thereof;
    partition walls extending upward from a top surface of the base and defining at least one leg channel extending substantially from the knee end to the foot end of the base and wherein the at least one leg channel is open between the partition walls at a knee end thereof and is open between the partition walls at a foot end thereof;
    wherein the at least one leg channel includes a foot portion at a foot end thereof having a width and depth configured to support the foot in a substantially upright orientation, and wherein an upper knee end of the at least one leg channel has a width greater than the width of the foot portion; and
    a heel opening in the base between the partition walls at the foot end of the at least one leg channel, the heel opening extending downward from the top surface of the base a distance configured such that when the leg is resting on the base inside the at least one leg channel, the heel extends down into the heel opening and is supported above a bottom of the heel opening by the leg resting on the top surface of the base.

2. The apparatus of claim 1 wherein a floor of the at least one leg channel tapers upward from the knee end thereof to the foot portion thereof.

3. The apparatus of claim 1 wherein the at least one leg channel tapers outward from an upper end of the foot portion thereof such that the leg channel is wider at the knee end thereof than at the foot portion thereof.

4. The apparatus of claim 1 comprising right, left, and middle partition walls defining right and left leg channels.

5. The apparatus of claim 4 wherein the top surface of the base forms a floor of each of the right and left leg channels and tapers upward from the corresponding knee end thereof to the foot portion thereof in each of the right and left leg channels.

6. The apparatus of claim 5 wherein the right and left leg channels taper outward from upper ends of the foot portions thereof such that the right and left leg channels are wider at the knee end of the base than at the foot portions thereof.

7. The apparatus of claim 4 wherein the foot portions of the leg channels have a width of about 2.5 inches to 3.5 inches, and a depth of about five inches to eight inches.

8. The apparatus of claim 7 wherein the foot portions have a length of about three inches to about five inches.

9. The apparatus of claim 4 wherein the heel recesses extend from the foot end of the base about 3 inches to 5 inches up the leg channels.

10. The apparatus of claim 4 wherein a distance from the knee end to the foot end of the base is about 21 inches to about 25 inches.

11. The apparatus of claim 1 wherein the base and partition walls are made from a resilient material.

12. The apparatus of claim 11 wherein the resilient material is one of a sponge material and a foam material.

13. The apparatus of claim 1 further comprising a washable pillow cover configured to conform to at least a top portion of the base, the partition walls, and the leg channels, and configured such that the pillow cover is removable.

14. The apparatus of claim 1 further comprising a foot drop strap adapted to be attached across a lower end of at least one foot portion, the foot drop strap configured to bear against a bottom of the foot and support the foot in a substantially upright orientation.

15. The apparatus of claim 1 further comprising a foot cage adapted to be attached over at least one foot portion, the foot cage configured to support a sheet above toes of the foot.

\* \* \* \* \*